(12) United States Patent
Panda et al.

(10) Patent No.: US 12,039,725 B2
(45) Date of Patent: Jul. 16, 2024

(54) SYSTEM AND METHOD TO GENERATE DISCRETIZED INTERPRETABLE FEATURES IN MACHINE LEARNING MODEL

(71) Applicant: Niramai Health Analytix Pvt. Ltd., Bangalore (IN)

(72) Inventors: Minerva Panda, Bhubaneswar (IN); Siva Teja Kakileti, Kakinada (IN); Geetha Manjunath, Bangalore (IN)

(73) Assignee: NIRAMAI HEALTH ANALYTIX PVT. LTD., Bangalore (IN)

( * ) Notice: Subject to any disclaimer, the term of this patent is extended or adjusted under 35 U.S.C. 154(b) by 380 days.

(21) Appl. No.: 17/588,018

(22) Filed: Jan. 28, 2022

(65) Prior Publication Data

US 2022/0237781 A1   Jul. 28, 2022

(30) Foreign Application Priority Data

Jan. 28, 2021   (IN) .............................. 202141003755

(51) Int. Cl.
*G06K 9/00* (2022.01)
*G06T 7/00* (2017.01)
*G06V 10/25* (2022.01)
*G06V 10/764* (2022.01)
*G06V 10/82* (2022.01)
*G16H 15/00* (2018.01)

(52) U.S. Cl.
CPC ............ *G06T 7/0012* (2013.01); *G06V 10/25* (2022.01); *G06V 10/764* (2022.01); *G06V 10/82* (2022.01); *G16H 15/00* (2018.01); *G06T 2207/20081* (2013.01); *G06T 2207/20084* (2013.01); *G06T 2207/30068* (2013.01)

(58) Field of Classification Search
CPC ....... A61B 5/4528; A61B 6/00; A61B 5/0033; A61B 5/4509; A61B 5/7267; A61B 5/7275; A61B 5/7485; A61B 2576/00; A61B 6/5217; G06T 7/00; G16H 30/40; G16H 50/20; G16H 50/70
See application file for complete search history.

(56) References Cited

U.S. PATENT DOCUMENTS

| | | | |
|---|---|---|---|
| 2017/0245762 A1* | 8/2017 | Kakileti | B25J 19/023 |
| 2017/0249738 A1* | 8/2017 | Sivakumar | G16H 30/20 |
| 2017/0270659 A1* | 9/2017 | Venkataramani | G06T 7/11 |
| 2018/0000461 A1* | 1/2018 | Venkataramani | A61B 5/4312 |
| 2018/0000462 A1* | 1/2018 | Venkataramani | G06T 7/11 |

* cited by examiner

*Primary Examiner* — Dhaval V Patel

(57) ABSTRACT

A system and method for processing values of a subset of numeric features to provide interpretability of the results of a machine learning model, by determining an extent of the contribution of the subset of features towards a predicted class by performing: (i) receiving the thermal image, (ii) obtaining a region of interest in the thermal image of the subject, (iii) extracting a plurality of numeric features associated with the region of interest of the thermal image, (iv) predicting a class, (v) estimate an extent of contribution of the subset of numeric features towards the decision of the first machine learning prediction model (M) and (vi) generate a report that includes a generated discrete values that determines the extent of contribution of the subset of numeric features towards the predicted class.

10 Claims, 9 Drawing Sheets

| THE PLURALITY OF NUMERICAL VALUES REPRESENTING N CLUSTER CENTRES OR A PLURALITY OF PROBABILITY VALUES OF THE CLUSTER CENTRES 6002 | DISCRETE VALUES 6004 |
|---|---|
| LESS THAN OR EQUAL TO 15 (<=15) | 1 |
| 16-25 | 2 |
| 26-40 | 3 |
| 41-60 | 4 |
| 61-90 | 5 |
| 91-100 | 6 |
| 101-115 | 7 |
| 116-140 | 8 |
| 141-160 | 9 |
| GREATER THAN 160 (>160) | 10 |

FIG.6B

SYSTEM AND METHOD TO GENERATE DISCRETIZED INTERPRETABLE FEATURES IN MACHINE LEARNING MODEL

BACKGROUND

Technical Field

Embodiments herein is related to artificial intelligence-enabled medical diagnosis, and more particularly to a system and method for processing a plurality of numeric feature values extracted from a thermal image of a subject and determining an extent of contribution of subset of numeric features towards a predicted class.

Description of the Related Art

Artificial Intelligence (AI) enabled computer-aided tools are being employed in recent times in critical medical domains. Such advanced tools may be used by clinicians as a decision-making aid (e.g. for a second opinion) in clinical settings. While the AI-enabled tools are promising, the usage of AI and machine learning (ML) in medical imaging is a relatively new approach and many clinicians are still left to be convinced of its integration into clinical practices due to several impediments, the primary reason being low interpretability of the output of AI algorithms. In a critical use case such as in medical domain, this results in a gap in clinician's understanding of the reason for the decision of AI/ML algorithm's predictions and hence affects the believability and usability of the results of the algorithm. The AI/ML algorithm uses a wide variety of features for final prediction and the interpretability of these features plays an essential role for a clinician for an effective decision-making process. In some clinical practices such as cancer risk assessment from familial and clinical factors, the implications of features such as number of first-degree relatives, age at menarche etc. are well-known and it might be easy to understand the reason behind the predicted risk from the extracted features. But in oncology, the implications of feature values extracted from the AI-based analysis of digital images of a cancer patient may not be easily understood. These extracted features from digital images of a cancer patient might be non-linear, continuous and vary in different ranges (not bounded) making it very complex for end-users (e.g. clinicians) to understand and decide the severity of parameters causing the abnormality in the subject.

In several exemplary scenarios, the clinicians need to understand and be able to explain the extremity of the extracted features that may consequently promote greater trust towards algorithmically-generated diagnosis reports. The success of an AI-enabled computer-aided screening is in its greater adoption by clinicians by enabling them to explicitly understand the features deciding the inferences (e.g. report) generated by the artificial intelligent tool. However, the existing AI-based tools available in the market may not have the implementation to decide the inferences from the digital image of the patients to enable feature interpretability helping the clinicians in understanding the implications of the feature values towards the decision of the AI-enabled tool. With the advent of deep-learning, these features are further complex to understand as even the features are learnt based on statistical patterns in the training set, and the features may or may not have a semantic meaning as those features are not crafted by the developers.

Hence, there is a need for a system to improve interpretability in AI-based tools which can be enabled by transforming the continuous and dynamic range of feature values extracted from a captured medical image to a discrete-valued fixed grading scale where the likelihood of contribution of the feature values towards predicted class monotonically changes with the increasing discrete scores on the grading scale.

SUMMARY

In view of the foregoing, an embodiment herein provides a system for processing values of a subset of numeric features that are extracted from a thermal image of a subject, to provide interpretability of the results of a machine learning model by determining an extent of contribution of the subset of numeric features towards a predicted class. The system includes a storage device and a processor. The processor retrieving machine-readable instructions from the storage device which, when executed by the processor, enable the processor to: (i) receive the thermal image of a body of the subject, (ii) obtain a region of interest in the thermal image of the subject, (iii) extract a plurality of numeric features associated with the region of interest of the thermal image, (iv) predicting a class in the subject, by classifying the plurality of numeric features using a first machine learning prediction model (M), (v) estimate an extent of contribution of the subset of numeric features towards the decision of the first machine learning prediction model (M) by generating a discrete value in the range of 1 to n using a mapping function and (vi) generate a report that including of a generated discrete values that determine the extent of contribution of the subset of numeric features towards the predicted class of the first machine learning model (M). The thermal image is captured by at least one of a thermal imaging camera or a wearable device. The thermal imaging camera or the wearable device includes (a) an array of sensors that converts infrared energy into electrical signals on a per-pixel basis and (b) a specialized processor that processes a detected temperature values into at least one block of pixels to generate the thermal image. The discrete value indicates the extent of contribution of the subset of numeric features towards the predicted class obtained from the first machine learning prediction model (M).

In some embodiments, the plurality of numeric features and corresponding classes are provided as training data to the first machine learning prediction model (M) to train the first machine learning prediction model (M) for predicting the class. The training data is obtained from the storage device.

In some embodiments, the mapping function is a pre-trained machine learning model that is trained with a training set that consisting of values of the subset of numeric features and its corresponding discrete values in the range 1 to n.

In some embodiments, the extent of contribution of the subset of numeric features indicating likelihood of a predicted class label is maximum when the discrete value associated with those values of the subset of numeric features is high and the extent of contribution of the subset of numeric features indicating the likelihood of the predicted class label is minimum when the discrete value associated with those values of the subset of numeric features is low.

In some embodiments, the mapping function is a non-uniform step function that generates the discrete values by training one or more second machine learning models which is used to obtain the non-uniform step function that maps the values of the subset of numeric features into the discrete values.

In some embodiments, the one or more second machine learning models includes of a third machine learning model (N) and a fourth unsupervised machine learning model (C).

In some embodiments, the non-uniform step function is obtained by (i) training the third machine learning model (N) by providing the values of the subset of numeric features from the first machine learning prediction model (M) as training data, (ii) splitting the values of the subset of numeric features into two main classes using the plurality of classifier threshold values that is obtained from third machine learning model (N), (iii) determining n cluster centres, using a fourth unsupervised machine learning model (C), such that the values of the subset of numeric features are clustered with n/2 cluster centres being in class A and n/2 cluster centres in class B, (iv) sorting the n cluster centres on a basis of distance from a decision boundary of the third machine learning model (N) and mapping them to the discrete values (1 to n) representing each of the n cluster centres and (v) forming the non-uniform step function with two or more axes representing the cluster centres and their corresponding discrete values. The training data is obtained from the storage device. The two main classes include an abnormal class (A) and a normal class (B). The n represents a total number of cluster centres into which the values of the subset of numeric features are clustered into.

In some embodiments, the fourth unsupervised machine learning model (C) uses a plurality of probability values obtained from the third machine learning model (N) as a distance metric to cluster and determine n/2 cluster centres that are within each of the two main classes (A and B). The n represents a total number of cluster centres into which the values of the subset of numeric features are clustered into.

In some embodiments, the discrete values are generated using the trained mapping function by (i) retrieving a trained mapping function from a storage associated with the values of the subset of numeric features, (ii) determining a cluster centre that is close to a value of the subset of numeric features by calculating a distance between the cluster centre and the value of the subset of numeric features and (iii) obtaining a discrete value corresponding to a closest cluster centre. The mapping function includes of an index table of cluster centres and their discrete scores in the range of 1 to n. The discrete value indicates the extent of contribution of the value of the subset of numeric features towards the predicted level.

In some embodiments, the first machine learning prediction model (M) includes a neural network model. The system processes the values of the subset of numeric features extracted from the plurality of numeric features from any of layers of a neural network model used for predicting the class, and enabling the user to understand the implication of the subset of numeric features towards the predicted class.

In another aspect, a method for processing values of a subset of numeric features that are extracted from a thermal image of a subject to provide interpretability of the results of a machine learning model, by determining an extent of contribution of the subset of features towards a predicted class. The method includes: (i) receiving the thermal image of a body of the subject captured by at least one of a thermal imaging camera or a wearable device, (ii) obtaining a region of interest in the thermal image of the subject, (iii) extracting a plurality of numeric features associated with the region of interest of the thermal image, (iv) predicting a class, by classifying the plurality of numeric features using a first machine learning prediction model (M), (v) estimate an extent of contribution of the subset of numeric features towards the decision of the first machine learning prediction model (M) by generating a discrete value in the range of 1 to n using a mapping function and (vi) generate a report that including of the generated discrete values that determine the extent of contribution of the subset of numeric features towards the predicted class of the first machine learning model (M).

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIGS. 6B and 6C illustrate a table view and its graphical representation of non-uniform step function associated to at least one of the subset of numerical feature values representing n cluster centres or a plurality of probability values of the cluster centres according to some embodiments herein.

DETAILED DESCRIPTION OF PREFERRED EMBODIMENTS

Figure 1:
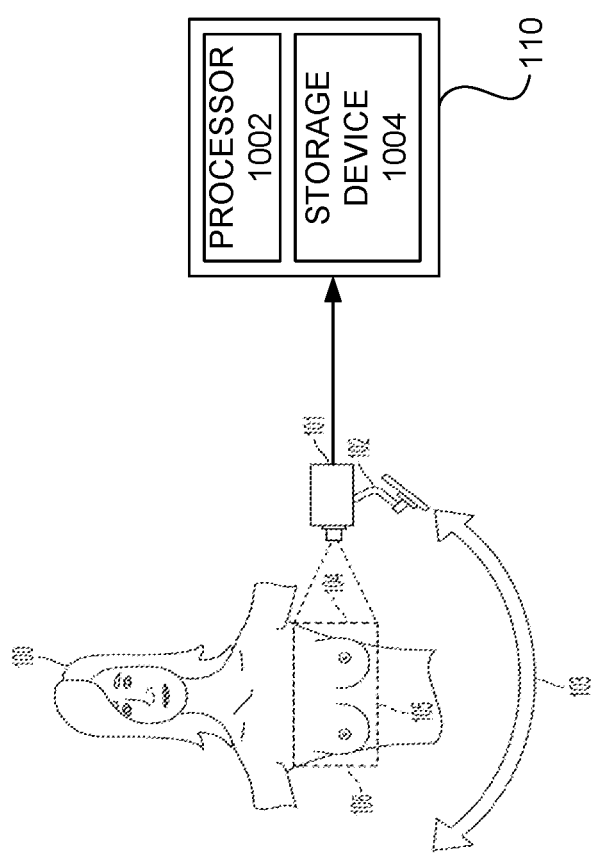
FIG. 1 illustrates an example subject with a thermal imaging camera mounted on a slidable and axially rotatable robotic arm for moving the thermal imaging camera along a semi-circular trajectory from side-to-side in front of the subject according to some embodiments herein.

The embodiments herein and the various feature values and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a system and method to transform a continuous and dynamic range of features values extracted from a thermal image of a subject to a fixed grading scale where likelihood of abnormality monotonically increases/decreases corresponding the increase/decrease (respectively) discrete scores on the grading scale. Referring now to the drawings, and more particularly to FIGS. 1 through 7, where similar reference characters denote corresponding feature values consistently throughout the figures, there are shown preferred embodiments.

A "person" refers to either a male or a female. Gender pronouns are not to be viewed as limiting the scope of the appended claims strictly to females. Moreover, although the term "person" or "patient" or "subject" is used interchangeably throughout this disclosure, it should be appreciated that the person undergoing screening may be something other than a human such as, for example, a primate. Therefore, the use of such terms is not to be viewed as limiting the scope of the appended claims to humans.

A "body" refers to a tissue of the body that is deemed appropriate for identifying the abnormality in the subject. It should be appreciated that the mediolateral.

FIG. 1 shows the body of a subject 100. It should be appreciated that the patient may be stationary while the camera moves about the patient, or the patient can move while the camera remains stationary, or the patient and the camera may move to capture the appropriate view angles as desired.

A "thermal camera" refers to either a still camera or a video camera with a lens that focuses infrared energy from objects in a scene onto an array of specialized sensors which convert infrared energy across a desired thermal wavelength band into electrical signals on a per-pixel basis and which output an array of pixels with colours that correspond to temperatures of the objects in the image.

A "thermographic image" or simply a "thermal image" is an image captured by a thermal camera. The thermographic image comprises an array of color pixels with each color being associated with temperature. Pixels with a higher temperature value are displayed in the thermal image in a first color and pixels with a lower temperature value are displayed in a second color. Pixels with temperature values between the lower and higher temperature values are displayed in gradations of color between the first and second colors.

"Receiving a thermal image" of a patient for determining the abnormality in the patient is intended to be widely construed and includes retrieving, capturing, acquiring, or otherwise obtaining video image frames.

"Analysing the thermographic image" means to identify one or more points (PN) in the image.

"Predicted class" referred to one or more classes associated to at least one of a state of tissue or a type of tissue. In some embodiments, the one or more classes includes at least one of benign lesion, malignant lesion or normal lesion.

FIG. 1 illustrates an example subject 100 with a thermal imaging camera 101 mounted on a slidable and axially rotatable robotic arm 102 for moving the thermal imaging camera 101 along a semi-circular trajectory from side-to-side in front of the subject 100 according to some embodiments herein. The thermal imaging camera 101 is mounted on the slidable and axially rotatable robotic arm 102 capable of moving the thermal imaging camera 101 along a semi-circular trajectory in front of the patient/subject 100 from side-to-side for capturing thermographic images. In some embodiments, the thermographic images may be captured in a right-side view 106, a front view 105, and a left-side view 104, and various oblique angles in between. In some embodiments, (i) a thermal image of the body of the subject 100 with highest temperature value displayed in a first color, (ii) the thermal image of the body of the subject 100 with lowest temperature value displayed in a second color, (iii) the thermal image of the body of the subject 100 between low and highest temperature value is displayed in gradations of color. In some embodiments, the thermal imaging camera 101 is communicatively connected to an abnormality prediction system 110. In some embodiments, the abnormality prediction system 110 includes (i) at least one processor 1002 and (ii) at least one storage device 1004. The processor 1002 receives the thermal image of the body of the subject 100. The storage device 1004 stores data corresponds to the received thermal image of the body of the subject 100 from the processor 1002. In some embodiments, the storage device 1004 stores the thermal imaging data. A resolution of the thermal imaging camera 101 is effectively the size of the pixel. Smaller pixels mean that the resulting thermal image have a higher resolution and thus better spatial definition. Although the thermal imaging camera 101 offers a relatively large dynamic range of temperature settings, the camera's temperature range should be relatively small, centered around the person's body surface temperature so that small temperature variations are amplified in terms of pixel color changes in order to provide a better measure of temperature variation. Thermal imaging cameras are readily available in various streams of commerce. In some embodiments, the thermal imaging camera 101 includes one or more sensors to convert infrared energy into electrical signals. In some embodiments, the thermal imaging camera 101 includes a lens that focuses the infrared energy from the body of the subject 100 and a specialized processor that processes the detected temperature values into at least one block of pixels to generate the thermal image. The abnormality prediction system 110 processes the thermal image captured by the thermal imaging camera 101 for processing a subset of numeric feature values of a first machine learning prediction model (M) that are extracted from the thermal image of the subject 100, for enabling a user (e.g. a doctor or a physician) to understand the contribution of the subset of numeric feature values towards a predicted class in the subject 100.

Figure 2:
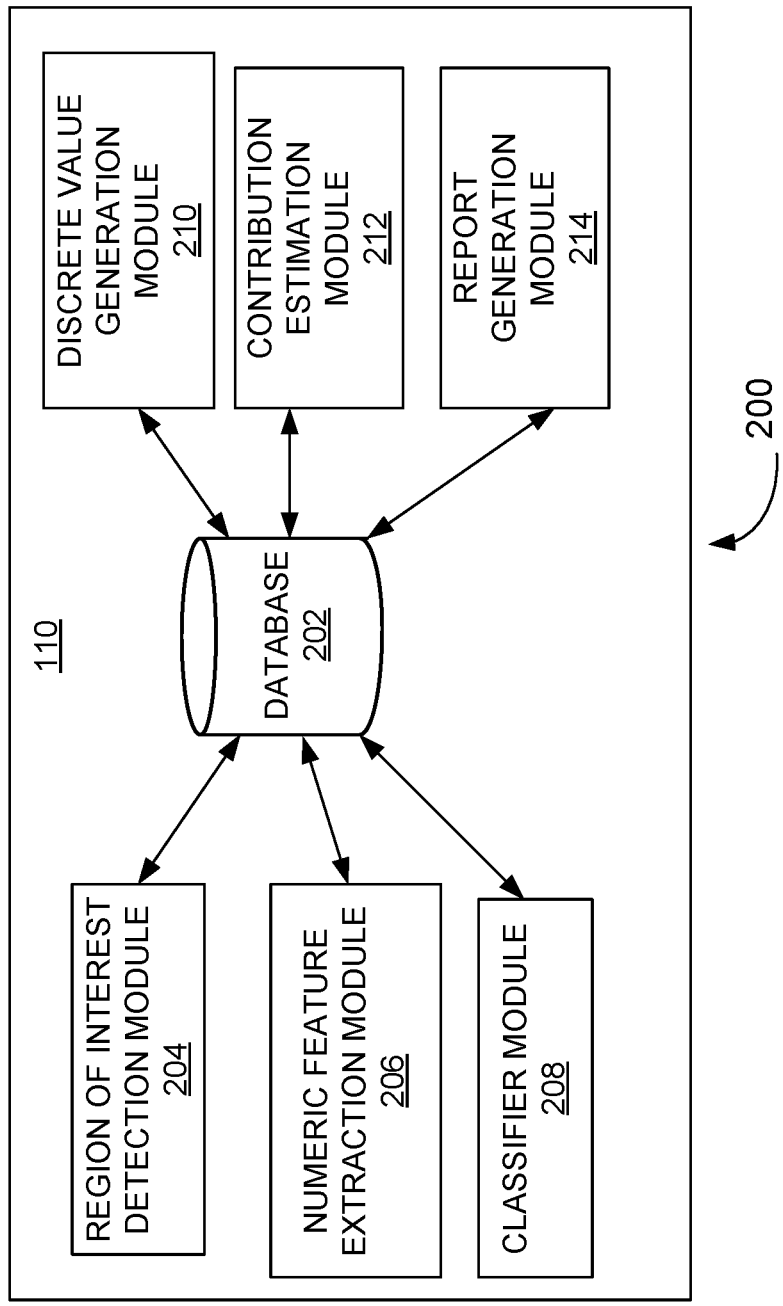
FIG. 2 illustrates an exploded view of an abnormality prediction system 110 for processing a subset of numeric features that are extracted from the thermal image of the subject using machine learning models according to some embodiments herein.

With reference to FIG. 1, FIG. 2 illustrates an exploded view of an abnormality prediction system 110 for processing a subset of numeric features that are extracted from the thermal image of the subject using machine learning models according to some embodiments herein. The exploded view 200 of the abnormality prediction system 110 includes a database 202, a region of interest detection module 204, a numeric feature extraction module 206, a classifier module 208, a discrete value generation module 210, a contribution estimation module 212 and a report generation module 214. In some embodiments, the thermal imaging camera 101 is communicatively connected to the abnormality prediction system 110. The thermal imaging camera 101 captures a thermal image of the body (e.g. a breast region) of the subject. In some embodiments, the thermal imaging camera 101 captures a particular region of the body of the subject. In some embodiments, the thermal image of the body of the subject is captured from a heat map of the body. In some embodiments, the thermal imaging camera 101 comprises a specialized processor that processes the captured thermal image of the body of the subject to generate a plurality of numeric feature values to detect the abnormality in the subject. The database 202 stores the captured thermal image of the body of the subject. The region of interest detection module 204 obtains the region of interest on the captured thermal image of the subject. In some embodiments, the region of interest on the thermal image of the subject is obtained using an automated segmentation technique. In some embodiments, the region of interest on the thermal image of the subject is obtained based on the input received from the user. The numeric feature extraction module 206 extracts a plurality of numeric features associated with the region of interest of the thermal image using at least one of an image processing technique or a mathematical analysis. In some embodiments, the plurality of numeric features (i) may be non-linear, (ii) may vary in different ranges or (iii) it may be complex to interpret its significance from the region of interest.

The classifier module 208 predicts a class by classifying the plurality of numeric features using a first machine learning prediction model (M). In some embodiments, the predicted class is related to one more classes that associated with a status of tissue of the subject. In some embodiments, the first machine learning prediction model (M) is trained using the plurality of numeric features and corresponding classes as training data. In some embodiments, the training data of the first machine learning prediction model (M) includes at least one of the plurality of numeric features, a plurality of probabilities or classes. In some embodiments, the training data is obtained from the storage device 1004. In some embodiments, the class may be predicted by a neural network model. The classifier module 208 identifies the values of the subset of numeric features from the plurality of numeric features classified by the first machine learning prediction model (M). In some embodiments, the first machine learning model (M) includes a neural network model. in some embodiments, the abnormality prediction system 110 processes the values of the subset of numeric features extracted from the plurality of numeric features from any of the layers of a neural network model for predicting the class. In some embodiments, the abnormality prediction system 110 enables the user to understand the implication of the subset of numeric features towards the predicted class using the classifier module 208.

The discrete value generation module 210 generates, using at least one of a mapping function or one or more second machine learning models, a discrete value for the subset of numeric features. In some embodiments, the discrete value indicates the extent of contribution of the subset of numeric features towards the predicted class obtained from the first machine learning prediction model (M). In some embodiments, the discrete value in a range from 1 to n. In some embodiments, the discrete value indicates the extent of contribution of the corresponding subset of numeric feature values towards the predicted class obtained from the first machine learning prediction model (M). The contribution estimation module 212 estimates the extent of contribution of the subset of numeric features towards the decision of the machine learning prediction model (M) using the generated discrete values in the range of 1 to n. In some embodiments, the extent of contribution of the subset of numeric features indicating a likelihood of a predicted class label is maximum when the discrete value associated with those values of the subset of numeric features is high. In some embodiments, the extent of contribution of the subset of numeric features indicating the likelihood of the predicted class label is minimum when the discrete value associated with that values of the subset of numeric features is low. In some embodiments, the extent of contribution of the subset of numeric features indicating the likelihood of the predicted class label is minimum when the discrete value associated with those values of the subset of numeric features is high and the extent of contribution of the subset of numeric features indicating the likelihood of the predicted class label is maximum when the discrete value associated with those values of the subset of numeric features is low. In some embodiments, the extent of contribution of the subset of numeric features indicates at least one of abnormality or normality in the subject.

The report generation module 214 generates a report with the generated discrete values that determine the extent of contribution of the subset of numeric features towards the predicted class of machine learning model (M). The abnormality prediction system 110 enables the user to understand the contribution of the subset of numeric features towards the predicted class. In some embodiments, the user may understand the contribution of the subset of numeric features towards the predicted class using the generated report.

Figure 3:
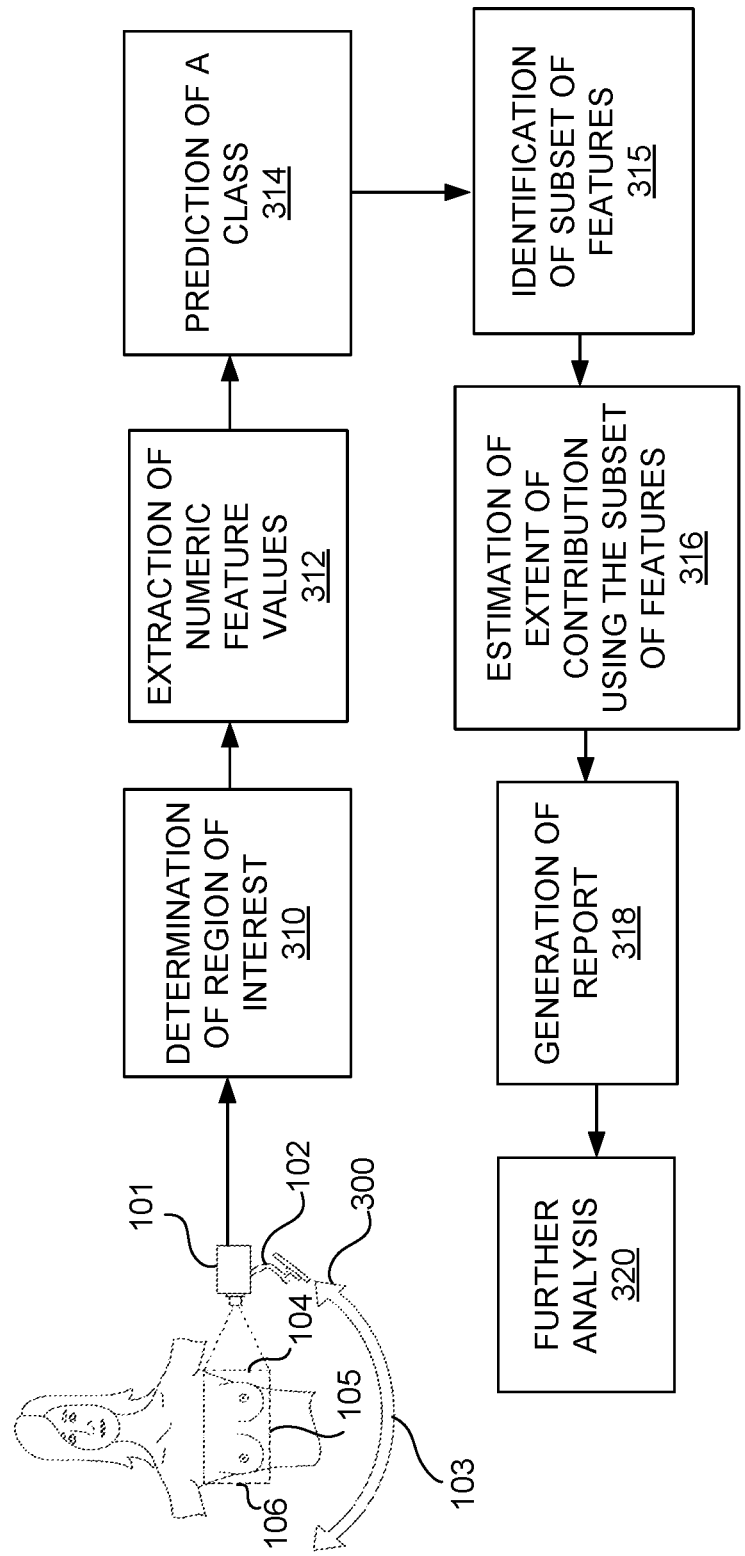
FIG. 3 illustrates an exemplary process flow of processing values of the subset of numeric features that are extracted from the thermal image of the subject, for determining an extent of a contribution of the subset of numeric features towards the predicted class according to some embodiments herein.
Figure 4:
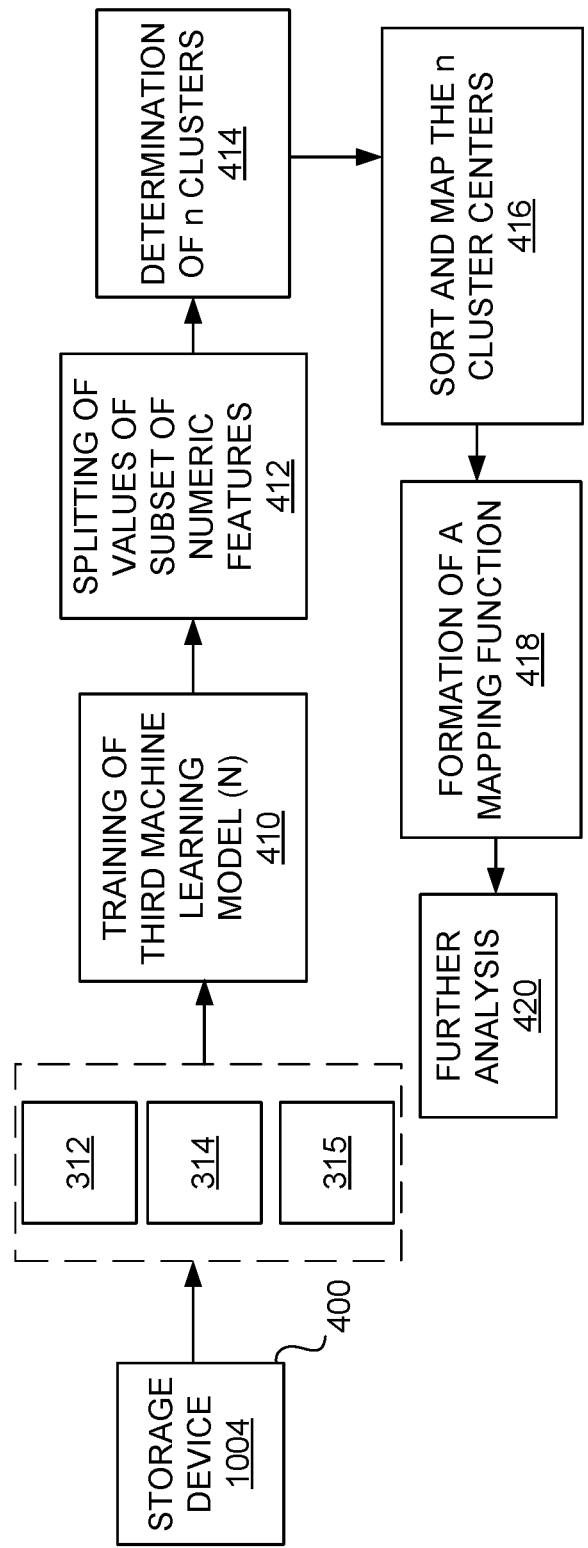
FIG. 4 illustrates an exemplary process flow of generation of discrete values using one or machine learning models according to some embodiments herein.
Figure 5:
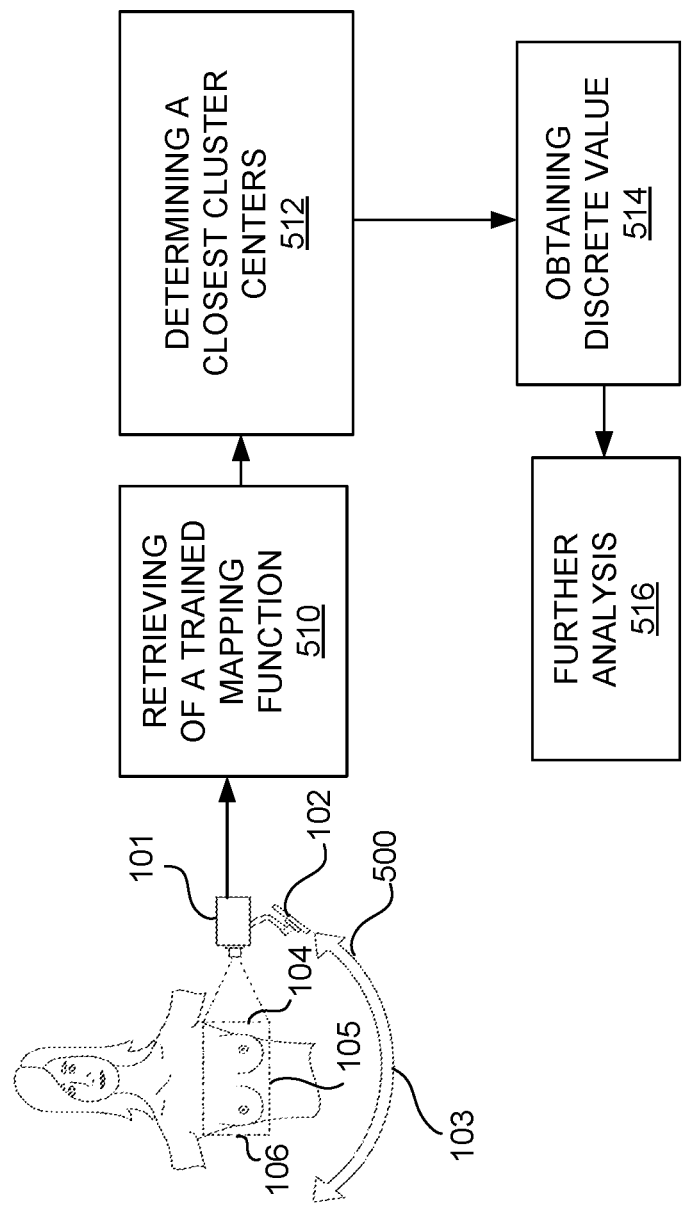
FIG. 5 illustrates an exemplary process flow of generation of discrete values using a mapping function according to some embodiments herein.

With reference to FIG. 1 and FIG. 2, FIG. 3 illustrates an exemplary process flow of processing values of the subset of numeric features that are extracted from the thermal image of the subject, for determining an extent of the contribution of the subset of numeric features towards the predicted class according to some embodiments herein. At step 300, the thermal image is captured using the thermal imaging camera 102. The thermal imaging camera 102 is mounted on a slidable and axially rotatable robotic arm 104 capable of moving the thermal imaging camera along a semi-circular trajectory in the front of the female patient/subject from side-to-side such that thermographic images may be captured in a right-side view 106, a front view 105, and a left-side view 104, and various oblique angles in between. In some embodiments, the thermal image may be received or retrieved from a remote device over a network, or from a media such as a CDROM or DVD. In some embodiments, the thermal image may also be received from an application such as those which are available for handheld cellular devices and processed on the cell phone or other handheld computing devices such as an iPad or Tablet-PC. In some embodiments, the thermal image may be received directly from a memory or a storage device of an imaging device that is used to capture the thermal image or a thermal video. In some embodiments, the thermal image is obtained by selecting a single image frame of the thermal video.

At step 310, the region of interest in the thermal image of the subject is determined using the region of interest detection module 204. In some embodiments, the region of interest on the thermal image is obtained from at least one of the user or through the automated segmentation technique. For example, the region of interest on the thermal image includes any location of the thermal image of the body of the subject captured in a right-side view 106, a front view 105, and a left-side view 104, and various oblique angles in between. At step 312, the plurality of numeric features associated with the region of interest of the thermal image is extracted using the image processing technique or the mathematical analysis. At step 314, the class is predicted by classifying the plurality of numeric features using a first machine learning prediction model (M). At step 315, subset of features is identified from the plurality of numeric features. At step 316, the abnormality prediction system 100 estimates the extent of contribution of the subset of numeric feature values by generating the discrete value in a range of 1 to n using one or more pretrained machine learning models and the subset of features. In some embodiments, the discrete value is generated in the range 1 to n for the values of the subset of numeric features using at least the mapping function or the one or more machine learning models. In some embodiments, the values of the subset of the numeric features are identified from the plurality of numeric features using the first machine learning modem (M). In some embodiments, the mapping function is a non-uniform step function and it generates the discrete values.

In some embodiments, the subset of numeric feature values and the predicted class obtained from the first machine learning prediction model (M) are processed by the one or more second machine learning models to generate discrete value. At step 318, the report is generated with the generated discrete values that determine the extent of contribution of the subset of numeric features towards the predicted class of machine learning model (M). At step 320, the generated report is provided to the abnormality prediction system 110 for further analysis.

With reference to FIG. 1 to FIG. 3, FIG. 4 illustrates an exemplary process flow of generation of discrete values using one or machine learning models according to some embodiments herein. At step 400, an image uploader receives the thermal image of the body of the subject captured by the thermal imaging camera 101 and uploads the thermal image of the body of the subject into the storage device 1004 for generating a mapping function for the subset of numeric feature values. In some embodiments, the mapping function converts the values of the subset of numeric features into the discrete value which indicates an extent of contribution of the subset of numeric features towards the predicted class that is generated by the first machine learning prediction model (M). In some embodiments, the one or more second machine learning models comprises of a third machine learning model (N) and a fourth unsupervised machine learning model (C). At step 410, the third machine learning model (N) is trained by providing the values of a subset of numeric features and the predicted class from the first machine learning prediction model (M) as training data. In some embodiments, the training data is obtained from the storage device 1004. At step 412, the values of the subset of numeric features are splitted into two main classes using the plurality of classifier threshold values that are obtained from the third machine learning model (N). In some embodiments, the two main classes include a class A and a class B. In some embodiments, the class A represents abnormality in the subject and the class B represents normality in the subject. At step 414, n cluster centers are determined using a fourth unsupervised machine learning model (C). The values of the subset of numeric features are clustered into n cluster centres such that n/2 cluster centres being in class A and n/2 cluster centres in class B. In some embodiments, the n represents a total number of cluster centers into which the subset of numeric feature values are clustered into. At step 416, the n cluster centres are sorted on a basis of distance from a decision boundary of the third machine learning model (N) and mapping them to the discrete values (1 to n) representing each of the n cluster centres.

At step 418, the non-uniform step function is formed with two or more axes representing the cluster centres and their corresponding discrete values. In some embodiments, the x-axis represents the n cluster centers and the y-axis represents the corresponding discrete values. At step 420, the mapping function is provided to the abnormality prediction system 110 for further analysis. In some embodiments, a third unsupervised machine learning model (C) includes any of a K Means, a Mean-Shift or density-based spatial clustering. In some embodiments, the machine learning models (M and N) includes any of a Support Vector Machine, a neural network, a Bayesian network, a Logistic regression, Naive Bayes, Randomized Forests, Decision Trees, Boosted Decision Trees, K-nearest neighbour, Neural Network Model or a Restricted Boltzmann Machine. In some embodiments, the fourth unsupervised machine learning model (C) includes any one of a K Means, a Mean-Shift or a density-based spatial clustering.

With reference to FIG. 1 to FIG. 3, FIG. 5 illustrates an exemplary process flow of generation of discrete values using a mapping function according to some embodiments herein. At step 500, an image uploader receives the thermal image of the body of the subject from the thermal imaging camera 101 and uploads the thermal image of the body of the subject into the one or more second machine learning models for generating the discrete values in the range of 1 to n. At step 510, a trained mapping function is retrieved from a storage associated with the values of the subset of numeric features. In some embodiments, the mapping function includes of an index table of cluster centres and their discrete scores in the range of 1 to n. At step 512, a cluster centre that is close to a value of the subset of numeric features is determined by calculating a distance between the cluster centre and value of the subset of numeric features. At step 514, a discrete value corresponding to a closest cluster centre is obtained. In some embodiments, the discrete value indicates the extent of contribution of the value of the subset of numeric features towards the predicted level. In some embodiments, the mapping function is a pretrained machine learning model that is trained with a training set that consisting of values of the subset of numeric features and its corresponding discrete values in the range 1 to n. At step 516, the discrete values are provided to the abnormality prediction system 110 or further analysis.

Figure 6A:
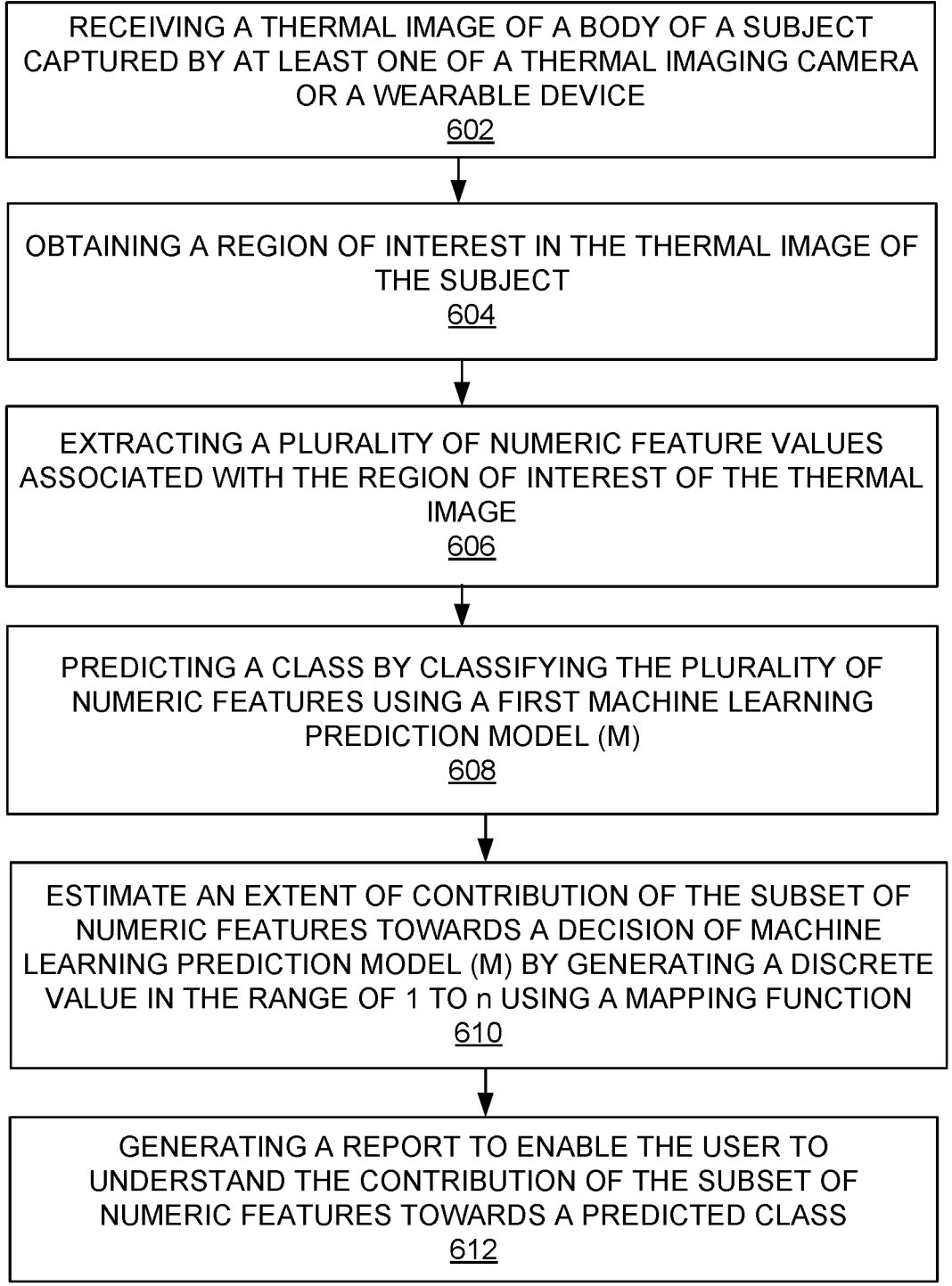
FIG. 6A illustrates a flow diagram that illustrates a method for processing values of a subset of numeric features that are extracted from a thermal image of the subject, for determining an extent of a contribution of the subset of numeric features towards a predicted class related to one or more classes in the subject according to some embodiments herein.

FIG. 6A illustrates a flow diagram that illustrates a method for processing values of a subset of numeric features that are extracted from a thermal image of the subject, for determining an extent of a contribution of the subset of numeric features towards a predicted class related according to some embodiments herein. At step 602, the thermal image of the body of the subject captured by at least one of a thermal imaging camera or a wearable device is received. A step 604, the region of interest in the thermal image of the subject is obtained from at least one of (i) the user or (ii) through an automated segmentation technique. At step 606, the plurality of numeric feature values associated with the region of interest of the thermal image is extracted using at least one of an image processing technique or mathematical analysis. At step 608, a class related is predicted by classifying the plurality of numeric features using a first machine learning prediction model (M). At step 610, the extent of contribution of the subset of numeric features towards the decision of machine learning prediction model (M) is estimated by generating a discrete value in the range of 1 to n using a mapping function. In some embodiments, the discrete value indicates the extent of contribution of the subset of numeric features towards the predicted class obtained from the first machine learning prediction model (M). At 612, the report is generated with the generated discrete values that determine the extent of contribution of the subset of numeric features towards the predicted class of machine learning model (M). In some embodiments, the abnormality prediction system 110 enables the user to understand the contribution of the subset of numeric features towards the predicted class.

Figure 6C:
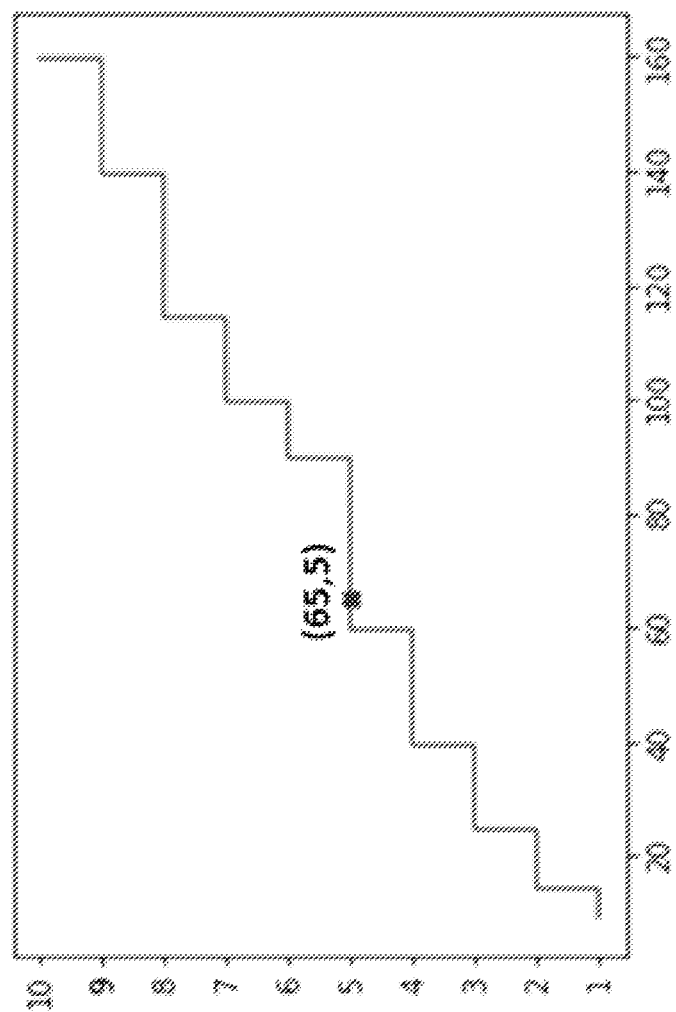

With reference to FIGS. 2, 6B and 6C illustrates a table view and its graphical representation of non-uniform step function associated to at least one of the subset of numerical feature value representing n cluster centres or a plurality of probability values of the cluster centres according to some embodiments herein. The table includes (i) a first field 6002 that comprises values associated with at least one of the subset of numeric feature values representing n cluster centres or the plurality of probability values of the cluster centres and (ii) a second field 6004 that includes discrete values associated to at least one of the subset of numeric feature values representing n cluster centres or a plurality of probability values of the cluster centres. In FIG. 6C, the graph comprises X axis representing the subset of numerical feature value representing n cluster centres and Y axis representing discrete values. The graph depicts discrete values associated to at least one of the subset of numerical feature value representing n cluster centres.

Figure 7:
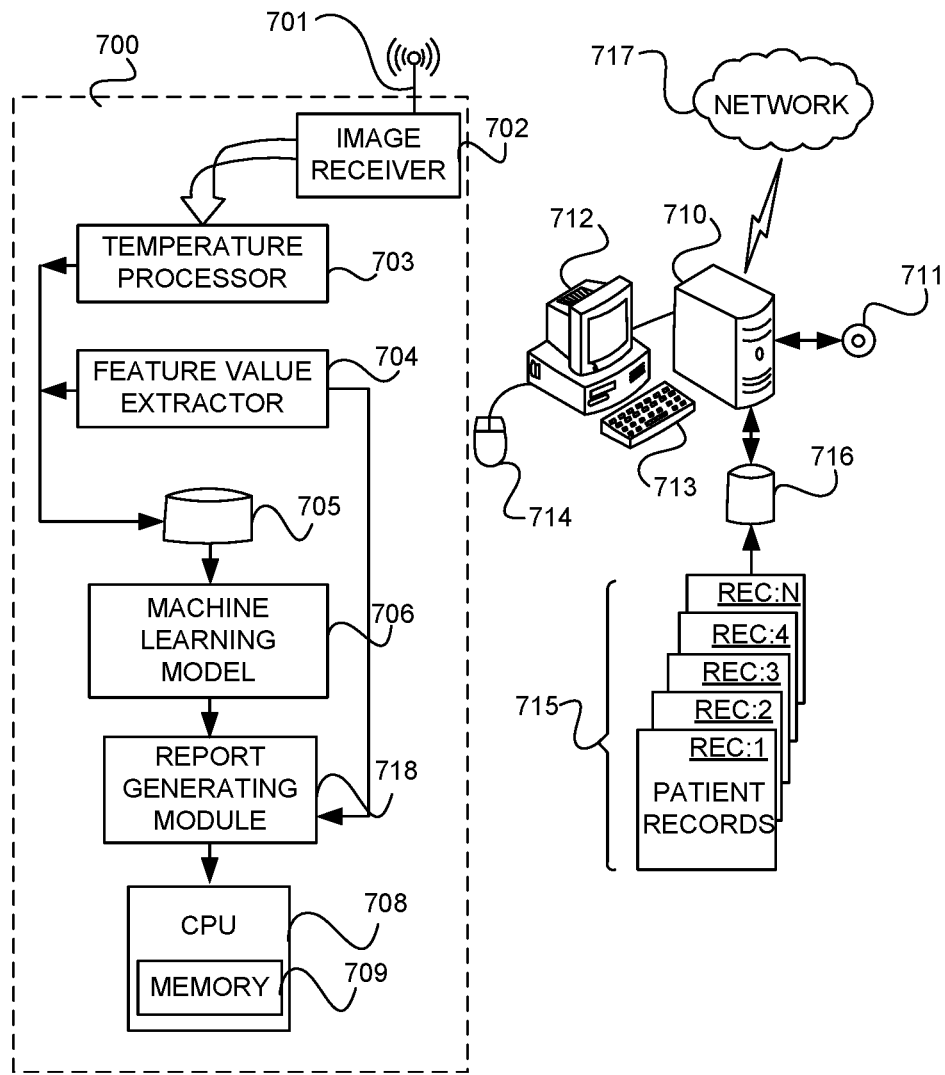
FIG. 7 illustrates a block diagram of one example system/image processing system for processing a thermal image in accordance with the embodiments described with respect to the flow diagram of FIG. 6A according to the embodiment herein.

FIG. 7 illustrates a block diagram of one example system/image processing system for processing a thermal image in accordance with the embodiments described with respect to the flow diagram of FIG. 6A according to the embodiment herein. The system includes an image receiver 702, a temperature processor 703, a feature value extractor 704, a storage device 705, a machine learning model 706, a Central Processing Unit (CPU) 708, a memory 709, a work station 710, a machine-readable media 711, a display device 712, a keyboard 713, a mouse 714, a database 716 and a network 717. The image Receiver 702 wirelessly receives the video via antenna 701 having been transmitted thereto from the video/thermal imaging camera 101 of FIG. 1. The temperate Processor 703 performs a temperature-based method to detect pixels in the received thermal image. The feature value extractor 704 extracts a plurality of feature values associated with the region of interest of the thermal image. Both Modules 703 and 704 store their results to the storage device 705. The machine learning model 706 retrieves the results from the storage device 705 and proceeds to process values of the subset of numeric features that are extracted from the thermal image of the subject, for enabling the user to understand the contribution of the subset of numeric features towards the predicted class. The machine learning model 706 predicts the class by classifying the plurality of numeric features and estimates the extent of contribution of the subset of numeric features towards the decision of machine learning prediction model (M). The report generating model 718 generate the report to the user. The Central Processing Unit (CPU) 708 retrieves machine-readable program instructions from the memory 709 and is provided to facilitate the functionality of any of the modules of the system 700. The Central Processing Unit (CPU) 708, operating alone or in conjunction with other processors, may be configured to assist or otherwise perform the functionality of any of the modules or processing units of the system 700 as well as facilitating communication between the system 700 and the workstation 710.

System 700 is shown having been placed in communication with the workstation 710. A computer case of the workstation houses various components such as a motherboard with a processor and memory, a network card, a video card, a hard drive capable of reading/writing to the machine-readable media 711 such as a floppy disk, optical disk, CD-ROM, DVD, magnetic tape, and the like, and other software and hardware needed to perform the functionality of a computer workstation. The workstation further includes a display device 712, such as a CRT, LCD, or touch screen device, for displaying information, images, view angles, and the like. A user can view any of that information and make a selection from menu options displayed thereon. Keyboard 713 and mouse 714 effectuate a user input. It should be appreciated that the workstation has an operating system and other specialized software configured to display alphanumeric values, menus, scroll bars, dials, slideable bars, pull-down options, selectable buttons, and the like, for entering, selecting, modifying, and accepting information needed for processing in accordance with the teachings hereof. The workstation is further enabled to display thermal images, the abnormality in the subject and the like as they are derived. A user or technician may use the user interface of the workstation to obtain the region of interest in the thermal image of the subject from at least one of (i) the user or (ii) through the automated segmentation technique, extract the plurality of numeric feature values associated with the region of interest of the thermal image using at least one of the image processing technique or the mathematical analysis, predict the class by classifying the plurality of numeric features, estimate an extent of contribution of the subset of numeric features and generate the report with the generated discrete values that determine the extent of contribution of the subset of numeric features towards the predicted class of machine learning model (M) and enable the user to understand the contribution of the subset of numeric features towards the predicted class, as needed or as desired, depending on the implementation. Any of these selections or inputs may be stored/retrieved to storage device 711. Default settings can be retrieved from the storage device. A user of the workstation is also able to view or manipulate any of the data in the patient records, collectively at 715, stored in database 716. Any of the received images, results, determined view angle, and the like, may be stored to a storage device internal to the workstation 710. Although shown as a desktop computer, the workstation can be a laptop, mainframe, or a special purpose computer such as an ASIC, circuit, or the like.

Any of the components of the workstation may be placed in communication with any of the modules and processing units of the system 700. Any of the modules of the system 700 can be placed in communication with the storage devices 705, 716 and 202 and/or computer-readable media 711 and may store/retrieve therefrom data, variables, records, parameters, functions, and/or machine-readable/executable program instructions, as needed to perform their intended functions. Each of the modules of the system 700 may be placed in communication with one or more remote devices over network 717. It should be appreciated that some or all of the functionality performed by any of the modules or processing units of the system 700 can be performed, in whole or in part, by the workstation. The embodiment shown is illustrative and should not be viewed as limiting the scope of the appended claims strictly to that configuration. Various modules may designate one or more components which may, in turn, comprise software and/or hardware designed to perform the intended function.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope.

What is claimed is:

1. A system for processing values of a subset of numeric features that are extracted from a thermal image of a subject to provide interpretability of the results of a machine learning model, by determining an extent of a contribution of the subset of numeric features towards a predicted class, wherein the system comprises:
    a storage device; and
    a processor retrieving machine-readable instructions from the storage device which, when executed by the processor, enable the processor to:
        receive the thermal image of a body of the subject, wherein the thermal image is captured by at least one of a thermal imaging camera or a wearable device, wherein the thermal imaging camera or the wearable device comprises:
            an array of sensors that converts infrared energy into electrical signals on a per-pixel basis; and
            a specialized processor that processes a detected temperature values into at least one block of pixels to generate the thermal image;
        obtain a region of interest in the thermal image of the subject;
        extract a plurality of numeric features associated with the region of interest of the thermal image;
        predicting a class in the subject, by classifying the plurality of numeric features using a first machine learning prediction model (M);
        estimate an extent of contribution of the subset of numeric features towards the decision of the first machine learning prediction model (M) by generating a discrete value in the range of 1 to n using a mapping function, wherein the discrete value indicates the extent of contribution of the subset of numeric features towards the predicted class obtained from the first machine learning prediction model (M); and
        generate a report that comprises generated discrete values that determine the extent of contribution of the subset of numeric features towards the predicted class of the first machine learning model (M).

2. The system as claimed in claim 1, wherein the plurality of numeric features and corresponding classes are provided as training data to the first machine learning prediction model (M) to train the first machine learning prediction model (M) for predicting the class, wherein the training data is obtained from the storage device.

3. The system as claimed in claim 1, wherein the mapping function is a pretrained machine learning model that is trained with a training set that consisting of values of the subset of numeric features and its corresponding discrete values in the range 1 to n.

4. The system as claimed in claim 1, wherein the mapping function is a non-uniform step function that generates the discrete values by training one or more second machine learning models which is used to obtain the non-uniform step function that maps the values of the subset of numeric features into the discrete values, wherein the extent of contribution of the subset of numeric features indicating a likelihood of a predicted class label is maximum when the discrete value associated with those values of the subset of numeric features is high and the extent of contribution of the subset of numeric features indicating the likelihood of the predicted class label is minimum when the discrete value associated with those values of the subset of numeric features is low.

5. The system as claimed in claim 4, wherein the one or more second machine learning models comprises of a third machine learning model (N) and a fourth unsupervised machine learning model (C).

6. The system as claimed in claim 4, wherein the non-uniform step function is obtained by:
    training the third machine learning model (N) by providing the values of the subset of numeric features from the first machine learning prediction model (M) as training data, wherein the training data is obtained from the storage device;
    splitting the values of the subset of numeric features using the plurality of classifier threshold values that is obtained from third machine learning model (N);
    determining n cluster centres, using a fourth unsupervised machine learning model (C), such that the values of the subset of numeric features are clustered with n/2 cluster centres being in class A and n/2 cluster centres in class B, wherein n represents a total number of cluster centres into which the values of the subset of numeric features are clustered into;
    sorting the n cluster centres on a basis of distance from a decision boundary of the third machine learning model (N) and mapping them to the discrete values (1 to n) representing each of the n cluster centres; and
    forming the non-uniform step function with two or more axes representing the cluster centres and their corresponding discrete values.

7. The system as claimed in claim 5, wherein the fourth unsupervised machine learning model (C) uses a plurality of probability values obtained from the third machine learning model (N) as a distance metric to cluster and determine n/2 cluster centres that are within each of the two main classes (A and B), wherein n represents a total number of cluster centres into which the values of the subset of numeric features are clustered into.

8. The system as claimed in claim 5, wherein the discrete values are generated using the trained mapping function by:
    retrieving a trained mapping function from a storage associated with the values of the subset of numeric features, wherein the mapping function comprises of an index table of cluster centres and their discrete scores in the range of 1 to n;
    determining a cluster centre that is close to a value of the subset of numeric features by calculating a distance between the cluster centre and the value of the subset of numeric features; and
    obtaining a discrete value corresponding to a closest cluster centre, wherein the discrete value indicates the extent of contribution of the value of the subset of numeric features towards the predicted level.

9. The system as claimed in claim 1, wherein the first machine learning prediction model (M) comprises a neural network model, wherein the system processes the values of the subset of numeric features extracted from the plurality of numeric features from any of layers of a neural network model used for predicting the class, and enabling the user to understand the implication of the subset of numeric features towards the predicted class.

10. A method for processing values of a subset of numeric features that are extracted from a thermal image of a subject to provide interpretability of the results of a machine learning model, by determining an extent of contribution of the subset of features towards a predicted class, wherein the method comprises:
- receiving the thermal image of a body of the subject captured by at least one of a thermal imaging camera or a wearable device;
- obtaining a region of interest in the thermal image of the subject;
- extracting a plurality of numeric features associated with the region of interest of the thermal image;
- predicting a class, by classifying the plurality of numeric features using a first machine learning prediction model (M);
- estimate an extent of contribution of the subset of numeric features towards the decision of the first machine learning prediction model (M) by generating a discrete value in the range of 1 to n using a mapping function, wherein the discrete value indicates the extent of contribution of the subset of numeric features towards the predicted class obtained from the first machine learning prediction model (M); and
- generate a report that comprising of generated discrete values that determine the extent of contribution of the subset of numeric features towards the predicted class of the first machine learning model (M).

* * * * *